US008888752B2

(12) United States Patent  
Cacka et al.

(10) Patent No.: US 8,888,752 B2  
(45) Date of Patent: Nov. 18, 2014

(54) BOTTLE FOR SINUS CAVITY RINSE

(75) Inventors: Joseph W. Cacka, Berthoud, CO (US); Kurt M. Taylor, Fort Collins, CO (US); Kenneth A. Hair, Fort Collins, CO (US); Brian R. Williams, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 92 days.

(21) Appl. No.: 12/970,788

(22) Filed: Dec. 16, 2010

(65) Prior Publication Data

US 2011/0139149 A1 Jun. 16, 2011

Related U.S. Application Data

(63) Continuation-in-part of application No. 29/352,091, filed on Dec. 16, 2009, now Pat. No. Des. 627,458, and a continuation-in-part of application No. 29/364,670, filed on Jun. 25, 2010.

(60) Provisional application No. 61/287,026, filed on Dec. 16, 2009, provisional application No. 61/369,378, filed on Jul. 30, 2010.

(51) Int. Cl.  
*A61M 31/00* (2006.01)  
*A61H 35/04* (2006.01)  
*A61M 3/02* (2006.01)

(52) U.S. Cl.  
CPC ............. *A61M 3/0262* (2013.01); *A61H 35/04* (2013.01); *A61M 3/0279* (2013.01); *A61M 2210/0618* (2013.01)  
USPC .......................................... 604/278; 604/514

(58) Field of Classification Search  
CPC .................. A61M 2210/0618; A61M 3/0262; A61M 3/0279; A61M 2205/075; A61M 2011/008; A61M 3/02; A61M 3/0233; A61M 3/0241; A61H 35/04; B05B 11/047; B05B 11/0016; A61K 9/0048  
USPC .......................... 604/264, 271, 275, 278, 279  
See application file for complete search history.

(56) References Cited

U.S. PATENT DOCUMENTS 465,559 A * 12/1891 Good ............................ 222/468  
2,115,959 A 5/1938 Lewis  
(Continued)

FOREIGN PATENT DOCUMENTS

DE 29602605 4/1996  
GB 881807 10/1958  
(Continued)

OTHER PUBLICATIONS

International Search Report, PCT/US2010/060880, 2 pages, Feb. 14, 2011.

(Continued)

*Primary Examiner* — Kevin C Sirmons  
*Assistant Examiner* — William Carpenter  
(74) *Attorney, Agent, or Firm* — Dorsey & Whitney LLP

(57) ABSTRACT

A vessel for use in rinsing a user's nasal cavities includes a main body, a spout, a self-sealing nozzle, and a flow control valve actuable by the user. The spout extends off of the main body and the elastomeric nozzle attached to the spout defines an outer skirt having a deflectable free end upon contact with the walls of the user's nasal cavity. A vacuum breaker valve is formed in a top portion of the main body for actuation by the user to control the flow of a fluid positioned in the vessel out of the nozzle. The main body may include gripping indentations along opposing sidewalls thereof. The spout may be integrally formed with the main body, and the spout and the nozzle may be detachably connected.

25 Claims, 10 Drawing Sheets

(56) References Cited

U.S. PATENT DOCUMENTS

| | | | |
|---|---|---|---|
| 2,224,296 A * | 12/1940 | Hoffman | 215/260 |
| 2,571,921 A | 10/1951 | Morris | |
| 2,578,864 A | 12/1951 | Tupper | |
| D169,996 S | 7/1953 | Vuillement | |
| 2,722,458 A | 11/1955 | Wahlin | |
| 2,811,283 A | 10/1957 | Bowen | |
| 2,987,261 A * | 6/1961 | McCuiston et al. | 239/304 |
| 3,176,883 A * | 4/1965 | Davis, Jr. | 222/633 |
| 3,363,808 A | 1/1968 | Gorman | |
| 3,455,294 A | 7/1969 | Adler et al. | |
| 3,820,532 A | 6/1974 | Eberhardt et al. | |
| 3,847,145 A | 11/1974 | Grossan | |
| 4,083,840 A | 4/1978 | Schoefberger | |
| D250,546 S | 12/1978 | Pick et al. | |
| D250,601 S | 12/1978 | Pick et al. | |
| 4,179,051 A | 12/1979 | Thomas | |
| 4,210,255 A * | 7/1980 | Pan | 220/203.15 |
| 4,356,941 A | 11/1982 | McRoskey et al. | |
| D271,028 S | 10/1983 | Adams | |
| 4,410,110 A * | 10/1983 | Del Bon et al. | 222/402.24 |
| 4,432,496 A | 2/1984 | Ito | |
| 4,439,206 A | 3/1984 | Hildebrand et al. | |
| 4,489,535 A | 12/1984 | Veltman | |
| 4,513,891 A * | 4/1985 | Hain et al. | 222/213 |
| 4,526,797 A | 7/1985 | Stone, Jr. | |
| 4,555,469 A | 11/1985 | Erdmann et al. | |
| 4,760,937 A * | 8/1988 | Evezich | 222/95 |
| 4,828,149 A | 5/1989 | Hester | |
| D305,262 S | 12/1989 | Nichols | |
| 4,925,128 A | 5/1990 | Brody | |
| D314,702 S | 2/1991 | Gonzalez | |
| D317,940 S | 7/1991 | Brenner | |
| 5,110,051 A | 5/1992 | Bennett | |
| 5,121,590 A * | 6/1992 | Scanlan | 53/510 |
| 5,125,543 A | 6/1992 | Rohrabacher et al. | |
| 5,127,553 A | 7/1992 | Weinstein | |
| 5,183,186 A | 2/1993 | Delaney, Jr. | |
| 5,301,846 A * | 4/1994 | Schmitz | 222/211 |
| 5,316,054 A | 5/1994 | Hall et al. | |
| 5,328,099 A | 7/1994 | Petit et al. | |
| 5,330,634 A | 7/1994 | Wong et al. | |
| 5,354,849 A | 10/1994 | Schoefberger | |
| 5,505,193 A | 4/1996 | Ballini et al. | |
| 5,570,966 A * | 11/1996 | Phelan | 401/183 |
| 5,611,376 A * | 3/1997 | Chuang | 141/65 |
| 5,649,530 A | 7/1997 | Ballini | |
| 5,655,686 A * | 8/1997 | Jermyn | 222/211 |
| D390,744 S | 2/1998 | Otero | |
| 5,806,723 A | 9/1998 | DuBose | |
| D405,525 S | 2/1999 | Barrett et al. | |
| 5,897,872 A | 4/1999 | Picciano | |
| 5,899,878 A | 5/1999 | Glassman | |
| 5,967,377 A | 10/1999 | Glynn | |
| 5,974,686 A * | 11/1999 | Nomura et al. | 34/263 |
| 6,006,952 A | 12/1999 | Lucas | |
| 6,035,769 A * | 3/2000 | Nomura et al. | 99/472 |
| D424,197 S | 5/2000 | Sydlowski et al. | |
| D426,300 S | 6/2000 | Conforti | |
| 6,135,358 A | 10/2000 | Ballini | |
| 6,238,377 B1 | 5/2001 | Liu | |
| 6,241,705 B1 * | 6/2001 | Ko-Wen | 604/73 |
| 6,293,436 B2 | 9/2001 | Faughnder et al. | |
| 6,520,384 B2 * | 2/2003 | Mehta | 222/211 |
| 6,540,718 B1 * | 4/2003 | Wennek | 604/94.01 |
| 6,558,344 B2 | 5/2003 | McKinnon et al. | |
| D481,794 S | 11/2003 | Krinsky | |
| 6,669,059 B2 | 12/2003 | Mehta | |
| D486,066 S | 2/2004 | Hannen et al. | |
| 6,688,497 B2 | 2/2004 | Mehta | |
| 6,736,792 B1 | 5/2004 | Liu | |
| D490,896 S | 6/2004 | Bogazzi | |
| D493,888 S | 8/2004 | Reschke | |
| D495,954 S | 9/2004 | Solomon | |
| D497,107 S | 10/2004 | Hama et al. | |
| 6,814,259 B1 | 11/2004 | Foster et al. | |
| 6,907,879 B2 | 6/2005 | Drinan et al. | |
| 6,976,669 B2 * | 12/2005 | Van Zijll Langhout et al. | 251/342 |
| 7,048,136 B2 * | 5/2006 | Havens et al. | 220/212 |
| D530,815 S | 10/2006 | Murphy et al. | |
| D538,474 S | 3/2007 | Sheppard et al. | |
| D548,334 S | 8/2007 | Izumi | |
| D550,097 S | 9/2007 | Lepoitevan | |
| 7,306,121 B2 * | 12/2007 | Ophardt et al. | 222/209 |
| D558,509 S | 1/2008 | Bodum | |
| D558,510 S | 1/2008 | Bodum | |
| D562,404 S | 2/2008 | Jansen et al. | |
| D584,151 S | 1/2009 | Murphy | |
| 7,500,584 B2 | 3/2009 | Shutz | |
| D590,493 S | 4/2009 | Harlan et al. | |
| D601,697 S | 10/2009 | Sobeich et al. | |
| D603,708 S | 11/2009 | Handy | |
| 7,621,416 B2 * | 11/2009 | Bursztein | 220/231 |
| D608,645 S | 1/2010 | Handy et al. | |
| D612,736 S | 3/2010 | Pecora | |
| D613,601 S | 4/2010 | Yoneda | |
| 7,703,696 B2 | 4/2010 | Eddins et al. | |
| D627,458 S | 11/2010 | Bisson et al. | |
| D629,884 S | 12/2010 | Stephens | |
| D630,314 S | 1/2011 | Stephens | |
| 7,862,536 B2 | 1/2011 | Chen et al. | |
| D634,213 S | 3/2011 | Thompson | |
| D634,630 S | 3/2011 | Taylor | |
| D634,631 S | 3/2011 | Taylor | |
| 7,959,597 B2 | 6/2011 | Baker et al. | |
| 7,971,761 B1 * | 7/2011 | Kudlu | 222/481.5 |
| D653,953 S | 2/2012 | Wakeman | |
| 8,113,832 B2 | 2/2012 | Snyder | |
| 2002/0158089 A1 | 10/2002 | Mehta | |
| 2003/0062367 A1 | 4/2003 | Robinson et al. | |
| 2003/0075542 A1 * | 4/2003 | Lin | 220/203.13 |
| 2005/0049620 A1 | 3/2005 | Chang | |
| 2006/0008373 A1 | 1/2006 | Schutz | |
| 2006/0253087 A1 | 11/2006 | Vlodaver et al. | |
| 2008/0008979 A1 | 1/2008 | Thomas et al. | |
| 2008/0294124 A1 | 11/2008 | Mehta | |
| 2009/0234325 A1 | 9/2009 | Rozenberg et al. | |
| 2009/0281454 A1 | 11/2009 | Baker et al. | |
| 2010/0152653 A1 * | 6/2010 | Hoke et al. | 604/94.01 |
| 2011/0084099 A1 | 4/2011 | Carta | |
| 2011/0139824 A1 | 6/2011 | Cacka et al. | |
| 2011/0139826 A1 | 6/2011 | Hair et al. | |
| 2011/0144588 A1 | 6/2011 | Taylor et al. | |
| 2011/0184341 A1 | 7/2011 | Baker et al. | |
| 2011/0319840 A1 | 12/2011 | Hair | |

FOREIGN PATENT DOCUMENTS

| | | |
|---|---|---|
| WO | WO9629044 | 9/1996 |
| WO | WO2005/000477 | 1/2005 |

OTHER PUBLICATIONS

International Search Report, PCT/US2010/060882, 2 pages, Feb. 16, 2011.
Author Unknown, "NasaFlo Neti Pot," http://www.neilmed.com/usa/nasaflo.php, 1 page, at least as early as Dec. 9, 2009.
Author Unknown, "SinuFlo Ready Rinse," http://www.neilmed.com/usa/sinuflo.php, 1 page, at least as early as Dec. 9, 2009.
Author Unknown, "Sinus Rinse Nasal Wash," http://www.neilmed.com/usa/sinusrinse.php, 3 pages, at least as early as Dec. 9, 2009.
Papsin et al., "Saline Nasal Irrigation," Canadian Family Physician, vol. 49, pp. 168-173, Feb. 2003.
Rabago et al., "Efficacy of Daily Hypertonic Saline Nasal Irrigation Among Patients with Sinusitis: A Randomized Controlled Trial," The Journal of Family Practice, vol. 51, No. 12, pp. 1049-1055, Dec. 2002.
Schumann et al., "Patients Insist on Antibiotics for Sinusitus? Here is a Good Reason to Say 'No'," The Journal of Family Practice, vol. 57, No. 7, pp. 464-468, Jul. 2008.

* cited by examiner

BOTTLE FOR SINUS CAVITY RINSE

CROSS-REFERENCE TO RELATED APPLICATIONS

This application claims the benefit of priority under 35 U.S.C. §120 as a continuation-in-part of U.S. design application No. 29/352,091 entitled "Vessel for sinus cavity rinse" filed 16 Dec. 2009 and as a continuation-in-part of U.S. design application No. 29/364,670 entitled "Faceted nasal seal" filed Jun. 25, 2010, the disclosures of which are hereby incorporated herein by reference in their entireties. This application claims the benefit of priority pursuant to 35 U.S.C. §119(e) of U.S. provisional application No. 61/287,026 entitled "Vessel for sinus cavity rinse" filed 16 Dec. 2009 and U.S. provisional application No. 61/369,378 entitled "Faceted nasal seal" filed 30 Jul. 2010, the disclosures of which are hereby incorporated herein by reference in their entireties.

This application is related to the application Ser. No. 12/970,610 entitled "Pot for sinus cavity rinse" filed contemporaneously herewith; the application Ser. No. 12/970,345 entitled "Powered irrigator for sinus cavity rinse" filed contemporaneously herewith; the application Ser. No. 12/970,854 entitled "Faceted nasal seal" filed contemporaneously herewith; and the application Ser. No. 12/970,415 entitled "Squeeze bottle for sinus cavity rinse" filed contemporaneously herewith, the disclosures of which are incorporated herein by reference in their entireties.

TECHNOLOGY FIELD

This disclosure relates to a vessel or vessels for nasal cavity rinse having a soft, self-sealing nozzle and a finger or thumb-actuated valve for controlling the flow of the liquid from the vessel.

BACKGROUND

The benefits of rinsing one's sinus cavities have been well established, and include improving resistance to sinus infections, clogged sinuses, allergies, and general health. Oftentimes, however, the articles which one uses to rinse their nasal passages make the process unnecessarily difficult and uncomfortable. One of the issues is related to the inability to obtain an effective seal between the nozzle of one of these articles and the user's nasal passage. If the seal is not adequate, during use the fluid can leak from between the nozzle and the nasal passage, thereby making the rinsing process messy.

In addition, the control of the flow from the vessel into the sinus cavity has not been adequate in the past, and users have found it difficult to regulate the volume of flow so as to make the rinsing process comfortable. In one existing product, as shown in U.S. App. Pub. No. 2008/0294124, an aperture is formed in the lid of the vessel which can be used to restrict the flow of the fluid in the vessel through the nozzle during the rinsing step. However, because the aperture is positioned in the lid, the user uses one hand to hold the vessel and another hand to control the flow by covering and uncovering the aperture. This proves to be a relatively difficult process when the user is already in an awkward position, such as being positioned over a sink during the rinsing process.

The information included in this Background section of the specification, including any references cited herein and any description or discussion thereof, is included for technical reference purposes only and is not to be regarded subject matter by which the scope of invention is to be bound.

SUMMARY

In one implementation, a vessel for use in rinsing a user's nasal passage includes a main body, a spout, an elastomeric nozzle attached to the spout, and a vacuum breaker for controlling the flow of a fluid within the vessel out of the nozzle.

In another implementation, a vessel includes a main body, a spout extending off the main body, an elastomeric nozzle attached to the spout, and a vacuum breaker valve formed in a top portion of said main body for actuation by the user to control the flow of a fluid positioned in the vessel out of the nozzle. The elastomeric nozzle defines an outer skirt having a free end that is deflectable upon engagement with the walls of the user's nasal cavity. The main body has gripping indentations along opposing sidewalls thereof.

In a further implementation, the vessel for use in rinsing a user's nasal passage includes a main body, a spout extending off a front portion the main body, an elastomeric nozzle detachably coupled to the spout, and a vacuum breaker valve formed in a top portion of said main body for actuation by the user to control the flow of a fluid positioned in the vessel out of the nozzle. The spout is integrally formed with the main body. The elastomeric nozzle defines an outer skirt having a free end and is deflectable upon engagement with the walls of the user's nasal cavity;

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the invention as claimed herein will be apparent from the following more particular written description of various embodiments of the invention as further illustrated in the accompanying drawings and defined in the appended claims.

DETAILED DESCRIPTION

Figure 1:
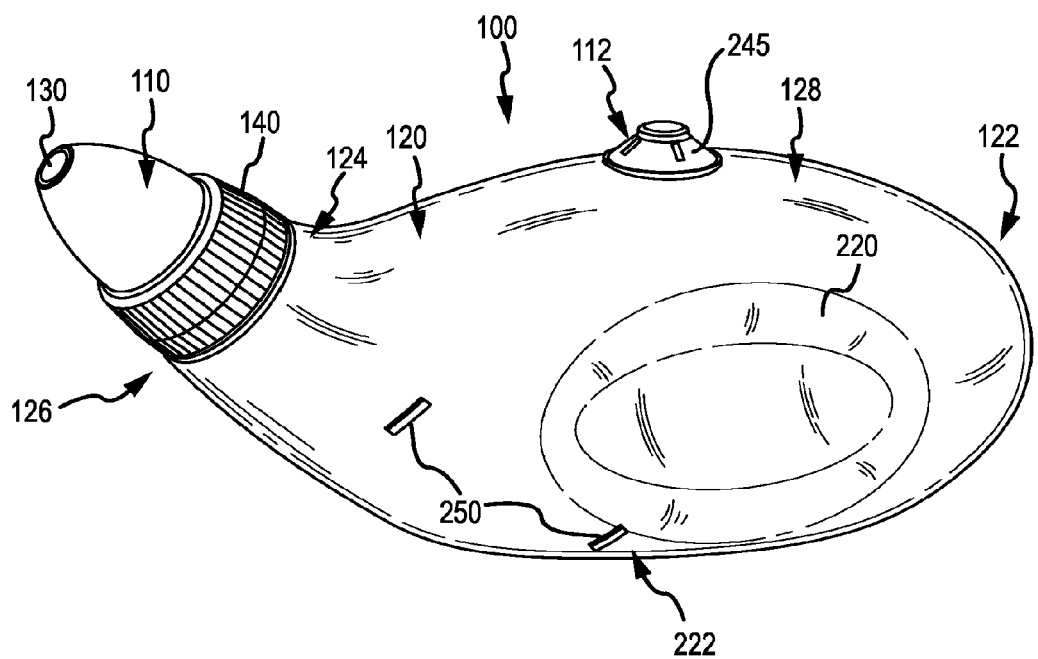
FIG. 1 is an isometric view of a vessel for use in rinsing a user's nasal cavities, and includes a body having a gripping portion, and a flow control valve, a spout, and a nozzle attached to the spout.

A vessel 100 for use in performing a sinus rinse is shown in FIGS. 1 through 8. The vessel 100 includes features that allow it to function in a beneficial manner for a user, including a self-sealing nozzle 110 and a vacuum breaker valve provided as a flow control valve 112.

FIGS. 1 through 6 show a bottle provided as a vessel 100 used for rinsing one's sinus cavities. The vessel shown in FIG. 1 has a main body 120 having an elongated shape which is wider than it is tall, with the elongated shape having a generally bulbous shape. One end of the bulbous shape is closed, forming a rounded back end 122 of the vessel, and a spout 124 is formed at the front portion 126 of the general bulbous shape. The spout 124 is angled upwardly from the main body 120 and terminates in a soft self-sealing nozzle 110 structure, described below. The flow control valve 112 is positioned at the upper surface 128 of the main body. The angled arrangement of the spout 124 and the placement of the flow control valve 112 allow the vessel 100 to be used for sinus rinsing so that the waste stream of water exiting a user's nostril does not come in contact with the main body 120 or the user's hand.

FIG. 1 shows the vessel 100 of the sinus rinsing article, which includes a main body 120 defining a cavity 121 for receiving a liquid, such as a sinus rinsing solution. A spout 124 is formed and extends off a front portion 126 of the main body 120 of the vessel with a self-sealing nozzle 110 positioned at a terminal end of the spout 124. The nozzle 110 includes an opening 130 through which the fluid inside the cavity 121 of the vessel may pass when the vessel 100 is tipped to allow the water to flow into the spout 124 and out of the nozzle opening 134. The spout 124, which includes an end portion 148 to which the nozzle 110 is attached, is open to and communicates with the cavity 121 of the main body 120.

Figure 2:
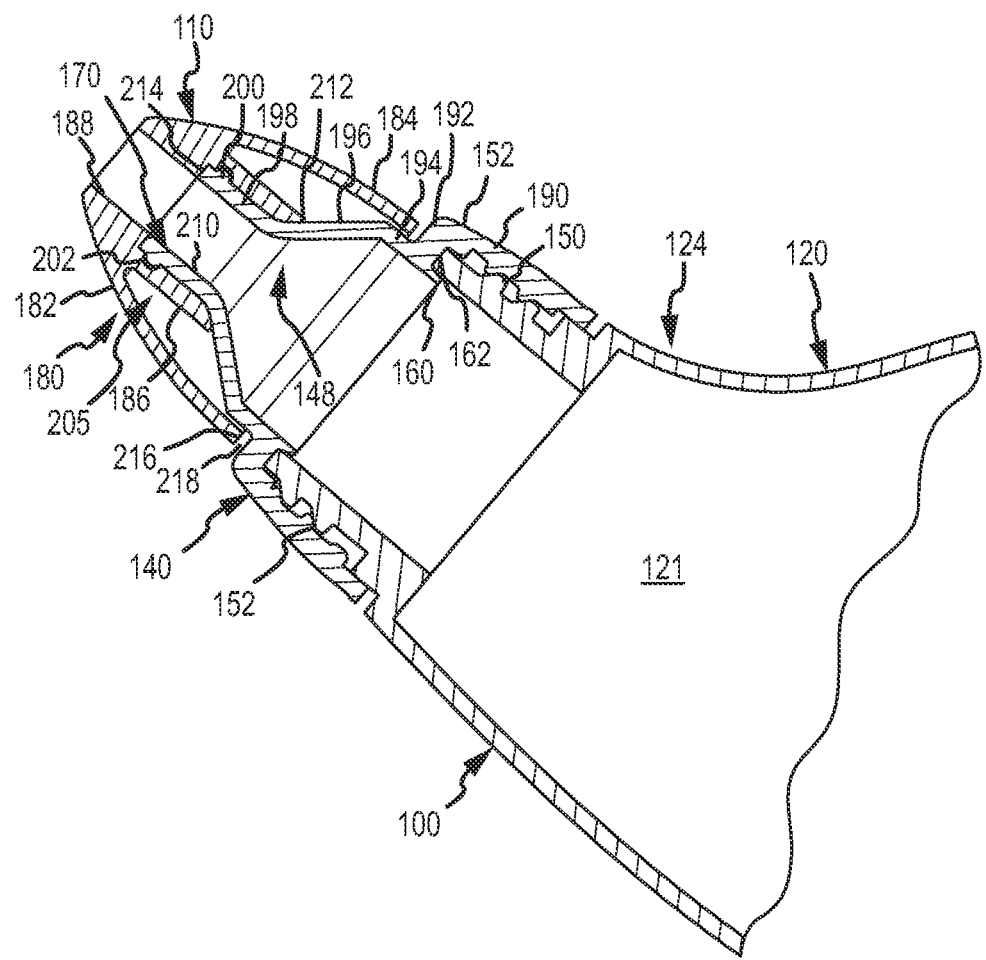
FIG. 2 is a cross-section view of the spout and nozzle of the vessel of FIG. 1.

FIGS. 1 and 2 show the soft self-sealing nozzle 110 structure that may be included on a cap 140 with an end portion 148. The cap 140 is formed as a separate piece threaded onto the main body 120. The spout 124 forms a threaded structure 150 for receiving a threaded collar 152 of the cap 140. The threaded engagement between the threaded collar 152 and the threaded structure 150 of the main body 120 forms an airtight and/or watertight seal by a sealing rim 160 of the threaded collar 152 contacting and surrounding the terminal end 162 of the threaded structure 150.

FIG. 2 shows an enlarged cross-section view of the self-sealing nozzle 110 connected with the end portion 148 of the spout 124. The self-sealing nozzle 110 has a main body 180, including the user engagement tip 182, an outer skirt 184 formed by a wall extending downwardly and outwardly away from the tip 182, and an inner collar 186 extending downwardly and away from the tip 182. An aperture 188 passes through the tip 182 and the inner collar 186. The inner collar 186 has a terminal edge, as does the outer skirt 184. The skirt 184 may be smoothly curved in the generally conically-shaped as shown, or may be faceted or otherwise made up of regions having flat extensions or mixed flat and curved extensions. Also, a rib may be formed around the skirt 184 wall just above the bottom edge to provide a protrusion for enhancing a user's gripping force on the nozzle 110 if necessary.

Also shown in FIG. 2 is the engagement structure 170 between the self-sealing nozzle 110 and the end portion 148 of the spout 124 to allow the nozzle 110 to be securely positioned on the spout 124 yet allow the nozzle 110 to self adjust its size to the size of the user's nasal passage during use, discussed in more detail below. This type of structure allows the nozzle 110 by itself to be removed from the engagement structure 170 for cleaning or replacement, and also allows the end portion 148 (with our without the nozzle 110) to be removed from the spout 124 to provide a larger opening for filling the vessel 100 from a faucet or other source.

The end portion 148 of the spout extends upwardly from the angled top surface of the spout 124 to receive the nozzle 110. The end portion 148 protrudes from the threaded collar 152 connected to the spout 124 and includes a base section 190 that forms an external portion of the threaded collar 152. The end portion 148 has a first diameter and a shoulder 192 formed annularly around the base section 190. The end portion 148 extends to a decreased diameter to form a first portion 194 of the end portion 148. The first portion 194 transitions into a conical section 196, which extends further away from the base section 190 and decreases the diameter even further until transitioning into a second portion 198. The second portion 198 forms a cylindrical wall and extends away from the conical section 196.

A sealing rim 160 is formed by an inner surface of the shoulder 192 and includes a protrusion depending downwardly from the shoulder 192 to form a sealing ring 160 that sealingly receives the terminal end 162 of the threaded structure 150 of the spout. An annular rib 200 is formed on the outer diameter of the second portion 198. The base section 190, the first portion 194, and the second portion 198 are generally cylindrical in shape, with the inner diameters and outer diameters being largest at the base section 190, somewhat smaller for the first portion 194, decreasing with the angle of the conical section 196, down to the size of the second portion 198.

The outer diameter of the second portion 198 that has the annular rib 200 is about the same diameter as the inner diameter of the inner collar 186 of the nozzle such that when the nozzle 110 is positioned over the second portion 198, the inner collar 186 of the nozzle engages the outer walls of the second portion 198. The rib 200 of the second portion snaps into the annular channel 202 formed in the inner diameter of the inner collar to hold the nozzle 110 onto the end portion 148 in a defined position. This engagement structure 170 allows secure placement of the nozzle 110 on top of the end portion 148, but allows the nozzle 110 to be removed for cleaning or replacement if desired.

When the nozzle 110 is positioned on the end portion 148, the aperture 188 of the engagement tip 182 of the nozzle 110 aligns with the aperture 210 formed in the second portion 198 of the end portion of the spout 124. The terminal edge 212 of the inner collar 186 of the nozzle 110 may engage the outer wall of the conical section 196 somewhat near the intersection between the conical section 196 and the second portion 198 of the end portion 148 of the spout 124. The terminal edge 212 of the inner collar 186 may be beveled at an angle complementary to the angle of the conical section 196 of the spout 124 to connect with the conical section 196 and to provide additional sealing. The engagement of the terminal edge 212 of the inner collar 186 provides sealing to help keep the fluid flowing through the end portion 148 and the nozzle 110 and from passing between the engagement of the nozzle 110 and the second portion 198. The end of the second portion 198 engages a shoulder 214 formed in the tip 182 of the nozzle, with the shoulder 214 being formed around the aperture 188 extending through the tip 182. The tip 182 of the nozzle 110 is solid in the area surrounding the aperture 188 extending through the tip 182.

An outer wall extends downwardly and away from the tip 182 to form a skirt 184, starting at about the position from where the inner collar 186 extends downwardly from the base of the tip 182. An annular spacing or void 205 is formed between the skirt 184 and the inner collar 186 and between the skirt 184 and the conical section 196. That is, the void 205 space is formed in the area of the nozzle 110 where the skirt 184 and inner collar 186 extend down. Because the wall forming the skirt 184 extends further from the tip 182 than the wall forming the inner collar 186 does, the void 205 is formed between the skirt 184 and conical section 196 beyond the terminal edge 212 of the inner collar 186.

The terminal edge 216 of the skirt 184 is positioned around the first portion 194 of the end portion of the spout 124. The terminal edge 216 of the skirt 184, as well as the adjacent wall structure of the skirt 184, closely fits with the first portion 194 of the end portion 148 but does not necessarily engage the first portion 194. Also, a gap 218 may be formed between the shoulder 192 extending between the base portion 190 and the first portion 194 and the terminal edge 216 of the skirt 184. The terminal edge 216 of the skirt 184 does not attach to or otherwise affix to the spout 124 and may move relative thereto. The inner collar 186 connects to the end portion 148 at a position closer to the tip 182 of the nozzle 110 and spaced above the edge of the skirt 184.

The nozzle 110 may be made of a soft elastomeric material, for example, food grade silicone rubber. The skirt 184, when positioned in the user's nasal passage, flexes inwardly into the void 205 and may do so irregularly around its circumference in order to closely match the shape of the user's nostril. This helps create an adequate seal between the user's nostril and the self-sealing nozzle structure. When the nozzle 110 is removed from the user's nostril, the elastomeric material springs back into its original shape. In one exemplary embodiment, he wall thickness of the skirt 184 may be 0.040 inches and the wall thickness of the inner collar 186 may be 0.060 inches. The gently curving, cone-like shape of the nozzle 110 from the tip 182 down to the terminal edge 216 of the skirt allows for a close fit with a variety of sizes of nasal passages. The void 205 space may be annular or may be discontinuous within the skirt 184.

One feature that allows the skirt 184 to provide an adequate seal for the user's nasal passages is the engagement of the terminal edge 216 of the skirt 184 with the first portion 194 of the end portion 148 of the spout 124. When the nozzle 110 is inserted into the user's nasal passage, and the skirt 184 compresses radially inwardly to conform to the shape of the user's nasal passage, the terminal edge 216 of the skirt 184 engages the first portion 194 of the end portion 148 of the spout and keeps that portion of the skirt 184 from deflecting further inwardly, thus providing some structural rigidity to the flexion of the portion of the skirt 184 extending between the tip 182 and the terminal edge 216. This provides some resistance to flexure to help create a firm but comfortable fit of the nozzle 110 within the user's nasal passage, and also facilitates the rebound of the skirt 184 back to its original shape after being removed from the user's nasal passage. However, the terminal edge 216 is not joined to the spout 124 and may move relative to the spout 124.

The longitudinal sides of the generally bulbous vessel 100 structure includes indentation regions 220 which provide gripping surfaces (gripping portions) for the user, as well as provide a unique aesthetic feature. The side indentations 220 help allow the user to comfortably hold the vessel 100 from above by grasping the sides with the thumb in one indentation region 220 and a finger(s) in the indentation region on the opposite longitudinal side of the sidewall to securely engage the vessel 100 during use. Similarly, the user may grasp the vessel 100 with the palm of the hand underneath the vessel with the fingers and thumb in the opposing indented regions.

The bottom 222 of the bulbous portion of the vessel 100 is relatively flat to allow upright orientation on a support surface, and the upper surface 128 of the longitudinal portion of the vessel is curved with a vacuum breaker valve provided as a flow control valve 112 situated at the top of the vessel 100 and near the center of its longitudinal length. However, the position of the flow control valve 112 could be at other locations in the vessel 100 not at the top and not at the center. Basically, the position of the flow control valve 112 as shown is beneficial for the intended uses. However, the flow control valve 112 can be positioned anywhere liquid will not flow out of when the vessel 100 is in use.

Figure 3:
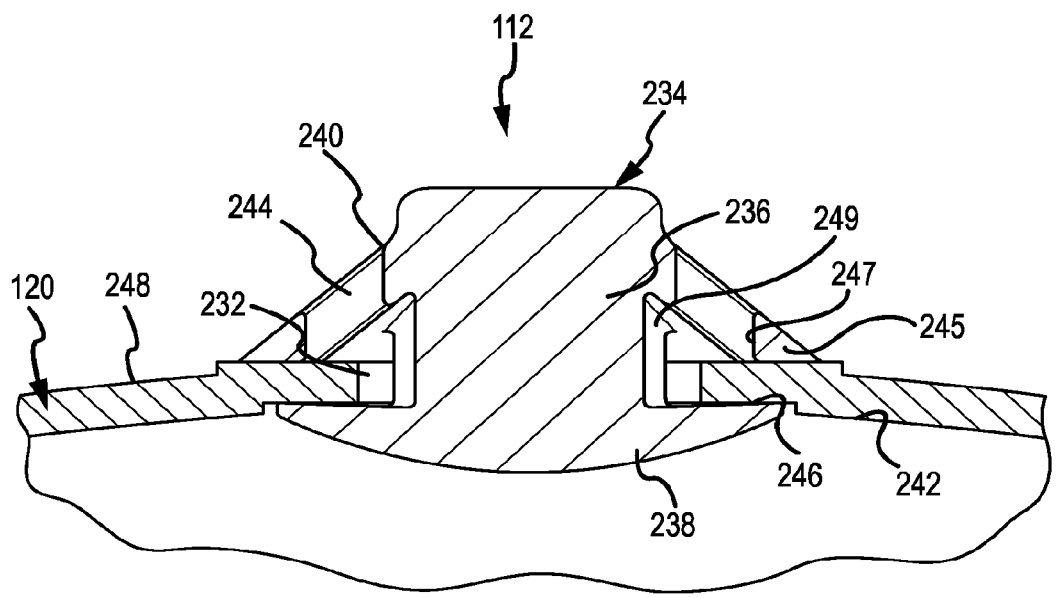
FIG. 3 is a cross-section view of the flow control valve in the closed position.
Figure 4:
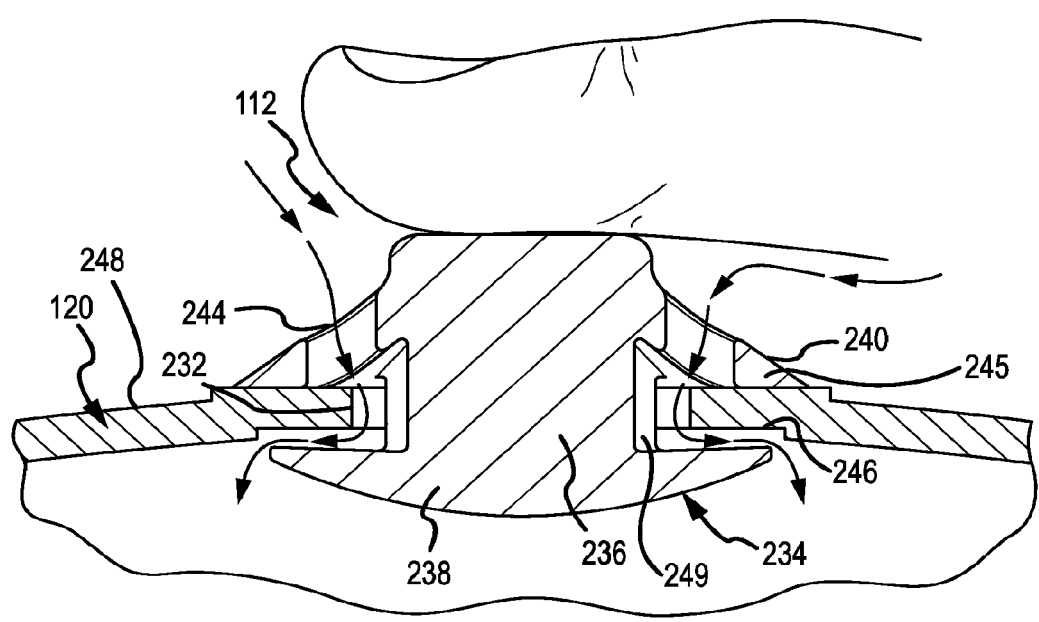
FIG. 4 is a cross-section view of the flow control valve in the open position.

FIGS. 3 and 4 show the operation of the flow control valve 112 (vacuum breaker) of the vessel 100. The flow control valve 112 is a combination of an aperture 232 formed in sidewall of the main body 120 of the vessel 100 and a resilient valve member 234 which, in its baseline position, is closed and, when actuated by the user, opens to allow air to flow into the cavity 121 of the main body of the vessel 100. FIG. 3 shows the valve member 234 in the closed or unactuated position. A seal is formed between the valve member 234 and the perimeter of the aperture 232. The valve member 234 has a valve body 236 having a generally cylindrical cross-section that extends vertically through the aperture 232 and two or more ribs 249 extend from the sides of the valve body 236. At the bottom end of the valve body 236, a flange 238 forming a curved disk shape extends peripherally around the valve body 236. At the top 248 of the valve body 236, a resilient top flange 240 extends downwardly and outwardly from the to 248 of the valve body 236 towards the periphery of the aperture 232, in a conical shape, and engages the main body 120 of the vessel 100 around the aperture 232 either continually or in discrete positions. This top flange 240 is positioned at an angle and extends downwardly from the valve body 236 to the periphery of the aperture 232, and provides the spring force for holding the valve member 234 in its closed position, whereby the lower flange 238 engages the periphery of the aperture 232 on the inside wall 242 of the main body 120 of the vessel 100 to create the seal. The to flange 240 has apertures 244 in its sides 245 to allow air through when the flow control valve 112 is open. Aperture sidewalls 247 defining the apertures 244 in the sides 245 of the flange are oriented such that they extend substantially perpendicularly relative to the top 128 of the main body 120.

In this closed position of the flow control valve 112 shown in FIG. 3, the lower flange 238 is engaged with a seat 246 formed around the aperture 232 on the inside wall 242 of the main body 120, thereby creating a seal and inhibiting the passage of air or liquid through the aperture 232. In this position, the to flange 240, which forms the spring force to hold the valve member in its closed position, is biasing the valve body 236 of the valve member upwardly through its resilient force created by pushing against the periphery of the top surface 248 of the main body 120 proximate the aperture 232. As shown in FIG. 4, the valve member 234 is actuated by the user pressing the valve body 236 downwardly through the aperture 232 against the force of the resilient top flange 240. The movement of the valve body 236 downwardly through the aperture 232 causes the sides 245 to splay outward along the top surface 128 of the main body 120 and disengages the peripheral flange 238 extending from the bottom of the valve body 236 and from the valve seat 246, which thus breaks the seal and allows air to flow into the cavity 121 of the main body 120. When air flows into the cavity 121 of the main body 120, the liquid in the cavity 121 of the main body is thus allowed to flow out of the nozzle 110 into the user's sinus cavities more freely and without restriction.

Figure 5:
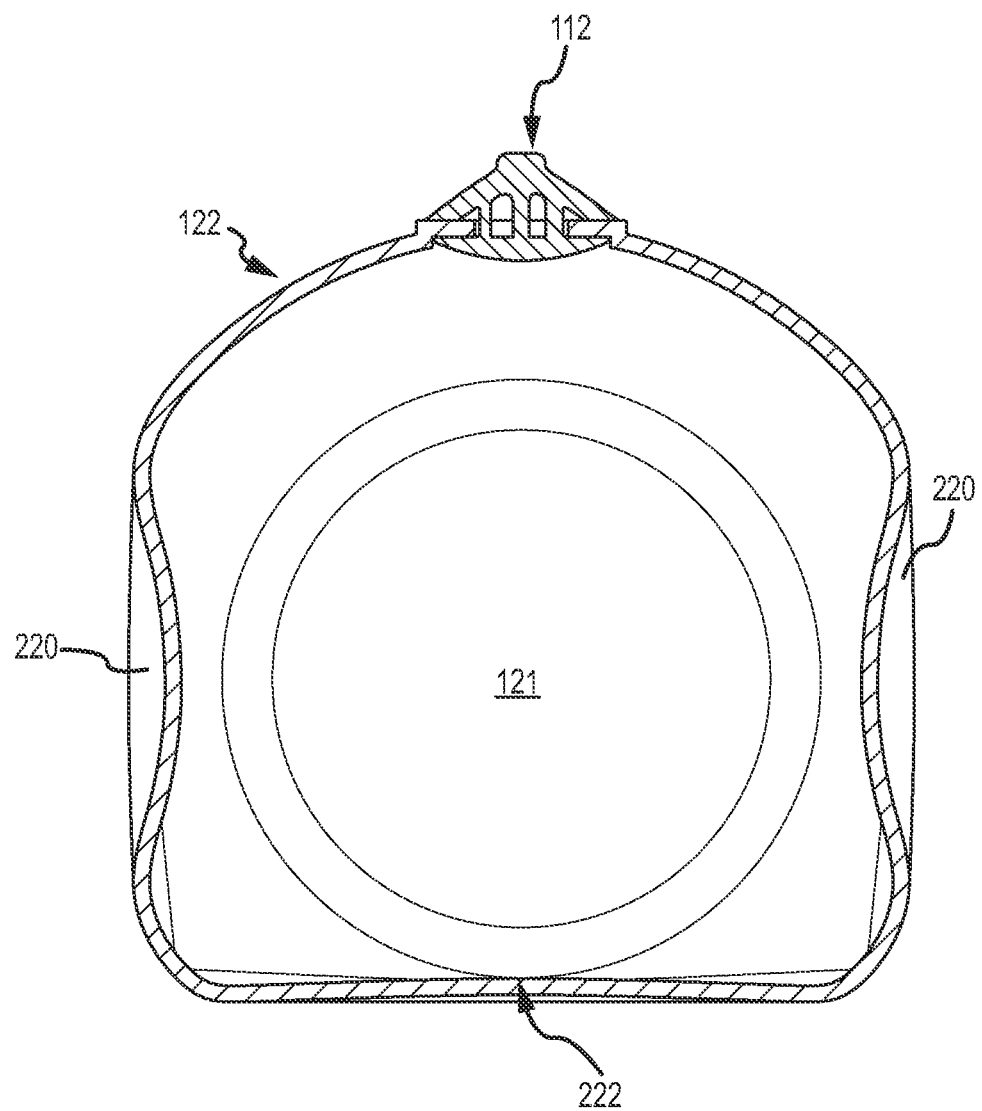
FIG. 5 is a cross-section view of the flow control valve showing the gripping portions formed in the sidewalls of the vessel.

The main body 120 of the vessel 100 may be made of high-density poly ethylene (HDPE) and may be blow-molded. The main body 120 may be opaque or translucent and may be relatively rigid enough for a user to grasp without the main body deforming significantly. FIG. 5 shows the indented sidewalls 220 of the vessel 100 which provide the unique aesthetic appearance as well as the finger grip benefit. As shown in FIG. 1, gradation marks 250 may be positioned on the outside of the main body 120 to provide the user with a measure of how much liquid is in the main body 120 when filling the vessel 100. Note that when the vessel 100 is being filled, it is typically being filled while held in the vertical position under a faucet. Thus, in one exemplary embodiment, the gradation markings may be oriented to allow for measurement, e.g., four ounces for the lower mark and eight ounces for the upper mark when held in the vertical position, not as measured when resting on its bottom 222 as shown in FIG. 1.

Figure 6:
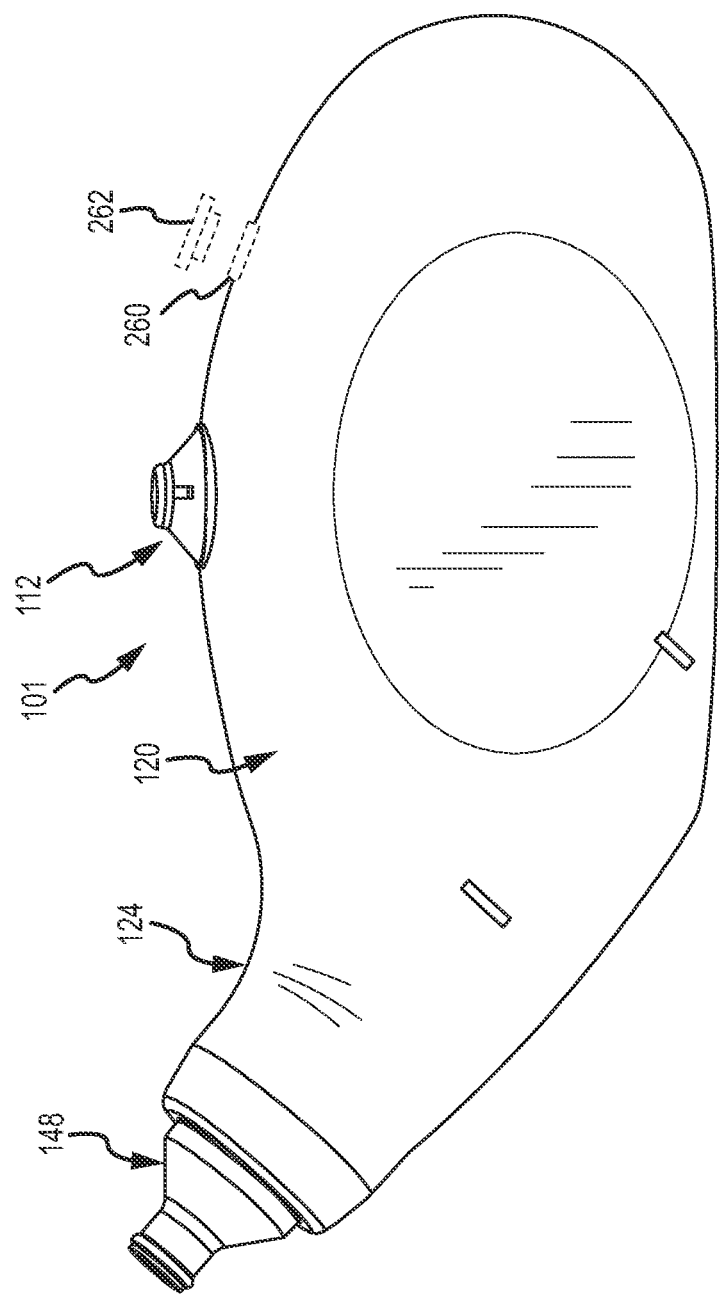
FIG. 6 is an isometric view of a vessel shown with the nozzle integrally formed with the main body.

FIG. 6 shows a vessel 101 according to an alternative embodiment in which the spout 124 and the end portion 148 are integrally formed. Accordingly, instead of the spout 124 forming a threaded structure 150 for receiving a cap 140 as shown in FIG. 2, the spout 124 extends from the front portion 126 of the main body 120 and forms the end portion 148. The spout 124 and end portion 148 may be formed integrally or may be nondetachably connected to one another. Other than being integrally formed, the structure and function of the spout 124 and its end portion 148 are substantially the same as described above, and would receive the nozzle 110 at the end portion 148. In addition, when the spout 124 and the end portion 148 are integrally formed, for example, the vessel 101 may optionally form an aperture 260 at a portion of the main body 120 to allow the vessel 101 to be filled via a larger opening compared to the aperture 188 of the nozzle. The aperture 260 of the main 120 body may have any size and shape and may be closed by a correspondingly configured cap 262. The connection between the aperture 260 and the cap 262 may be a threaded engagement, a sealing engagement, or another type of engagement that prevents fluid from leaking from the vessel 100 during use. In addition, sealing features such as o-rings and v-seals may be provided at the interface between the aperture 260 and the cap 262 to facilitate providing an airtight and/or watertight seal. The arrangement of the optional aperture 260 and the cap 262 may be provided at a portion of the main body 120 where a user's palm or finger would normally contact the main body 120 to provide manual sealing. In yet another embodiment, when the spout 124 and the end portion 148 are integrally formed, the resilient valve member 234 may be configured to be removable from the main body 120 allowing fluid to be poured into the aperture 232.

The arrangement of the flow control valve 112 on the top portion 128 of the main body allows the user to grasp the bottle at the sidewalls 220 so that the user's palm is proximate the back portion 122 of the main body and an index finger or thumb, for example, to be positioned above the flow control valve 112. The angled arrangement of the spout 124 and the nozzle 110 extending therefrom, allows the vessel 100 to be held and tipped downward as the nozzle is inserted into the user's nose. In this way, the nozzle 110 is lowered and the back portion 122 is raised. In this position, the user actuates the flow control valve 112, allowing fluid to exit the vessel 100, enter a user's first nostril and exit the user's second nostril. The angle of orientation of the vessel 100 allows the waste stream exiting the user's nostril to flow away from the vessel 100 and the user's hand holding the vessel 100.

Figure 7:
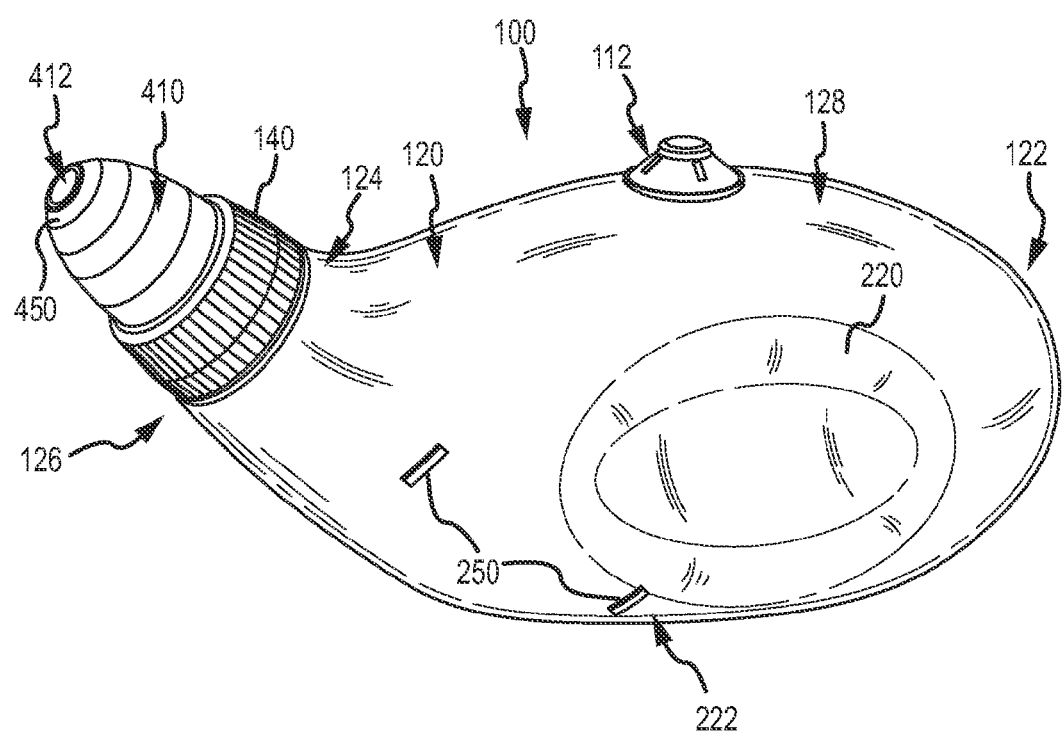
FIG. 7 is an isometric view of a vessel for use in rinsing a user's nasal cavities, and includes another embodiment of a nozzle.

FIG. 7 shows the vessel 100 with a faceted nozzle 410 having a faceted surface that allows the nozzle to create a seal within the nasal cavity better than an oval or purely round nozzle. As described further below in connection with FIGS. 8-10, the faceted or circumferentially stepped external surface of the nozzle 100 is made up of regions having flat extensions or mixed flat and curved extensions, as the faceted nozzle 410 extends downwards. Like the nozzle 110, the faceted nozzle 410 is self-sealing and may be made of a soft elastomeric material, for example, food grade silicone rubber. The faceted nozzle 410 includes an outlet aperture 412 formed at a center portion of the tip 450 or apex which is the first portion of the faceted nozzle 410 to enter the user's nostril when attached to the vessel 100. The faceted nozzle 410 may also be used in connection with the vessel 100.

Figure 8:
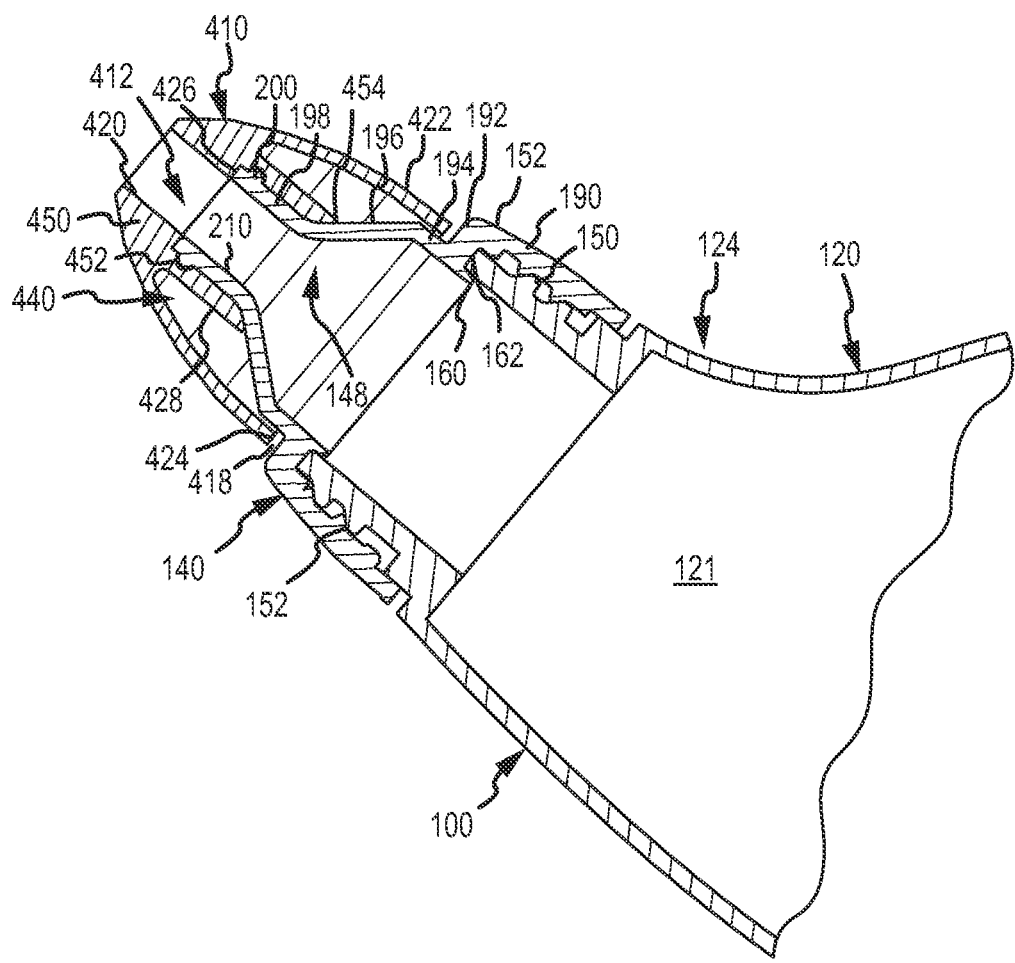
FIG. 8 is a cross-section view of the spout and nozzle of FIG. 7.

FIG. 8 is a cross-section view of the faceted nozzle 410 of FIG. 7 attached to the vessel 100 by the end portion 148 of the spout 124. The faceted nozzle 410 has an outer skirt 422 that extends outwardly and away from a tip 450, an inner collar 428 extending downwardly and away from the tip 450 and forms a cylindrical wall 420 creating a conduit or passageway within the inner surface of the faceted nozzle 410. The inner collar 428 may be formed integrally with the skirt 422. The inner collar 428 may terminate at the tip 450 creating the outlet aperture 412. The distal end of the inner collar 428 terminates inside the skirt 422. In some implementations the inner collar 428 may extend as far as the terminal edge 424 of the skirt 422 and in other implementations (such as the implementation illustrated in FIG. 8) the inner collar 428 may have a terminal edge 454 that terminates at a point above the terminal edge 424 of the skirt 422. In one exemplary embodiment, the wall thickness of the inner collar 428 may be approximately 0.060 inches.

As can be seen from FIG. 8, the inner collar 428 of the faceted nozzle 410 connects with the end portion 148 of the spout 124. The faceted nozzle 410 is placed above the end portion 148 and the end portion 148 may be inserted partially into the inner collar 428. In some implementations the end portion 148 may extend only partially into the inner collar 428. Furthermore, an o-ring (not shown) may be secured within the annular recess 452 to create a fluid-tight seal between the inner collar 428 and the end portion 148. The cap 140 is formed as a separate piece and is threaded onto the main body 120. The spout 124 forms a threaded structure 150 for receiving a threaded collar 152 of the cap 140. The threaded engagement between the threaded collar 152 and the threaded structure 150 of the main body 120 forms an airtight and/or watertight seal by a sealing rim 160 of the threaded collar contacting and surrounding the terminal end 162 of the threaded structure.

The skirt 422 extends away from the second portion 198 and the inner collar 428 creating a void 440 or open space between the conical section 196 of the end portion 148 and the skirt 422. The void 440 or annular spacing is also formed between the outer skirt 422 and the inner collar 428, and the wall forming the skirt 422 extends further from the tip 450 than does the wall forming the inner collar 428 such that the terminal edge 424 of the skirt 422 is positioned around a cylindrical first portion 194 of the end portion 148. The void space 440 may be annular and may be continuous or discontinuous within the skirt 422.

The terminal edge 424 of the skirt 422, as well as the adjacent wall structure of the skirt 422, may closely fit with the cylindrical first portion 194 of the end portion 148 of the spout 124, but not necessarily engage with the cylindrical first portion 194. Also, a small gap 418 may be formed between the shoulder 192 of the end portion 148 and the terminal edge 424 of the skirt 422. As discussed above, the terminal edge 424 of the skirt 422 may not attach to or otherwise be affixed to the cylindrical first portion 194 and may move relative thereto. In other implementations the outer skirt 422 may rest along the cylindrical first portion 194 or otherwise contact the cylindrical first portion 194 of the end portion.

The inner collar 428 extends downward from the outlet aperture 412 and may mate and fluidly connect with the end portion 148 of the spout 124, attaching the faceted nozzle 410 to the main body 120. The inner collar 428 may include an annular recess 452 along its inner walls to receive the circumferential rib 200 on the second portion 198 of the end portion 148 of the spout 124. The terminal edge 454 of the inner collar 428 may be beveled at an angle complementary to the angle of the conical portion 196 of the spout 124 to connect with the conical portion 196. The beveled terminal edge 454 may provide additional sealing and help keep the fluid flowing through the end portion 148 and the faceted nozzle 410 and prevent fluid from passing between the engagement of the faceted nozzle 410 and the second portion 198.

The tip 450 of the faceted nozzle 410 above the annular recess 452 extends down to a cylindrical wall 420 that defines the outlet aperture 412 and the tip 450 may be thicker than the wall of the inner collar 428. The inner collar 428 thus may have a larger inner diameter than the cylindrical wall 420 forming the outlet aperture 412. A shoulder 426 formed in the tip 450 of the faceted nozzle 410 may be formed around the aperture 412 and engage with the end of the second portion 198 of the end portion 148 of the spout 124.

Figure 9A:
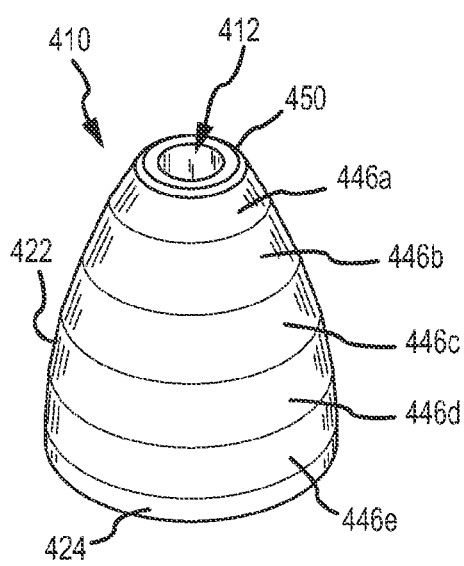
FIG. 9A is a top perspective isometric view of the nozzle of FIG. 7 removed from the vessel.
Figure 9B:
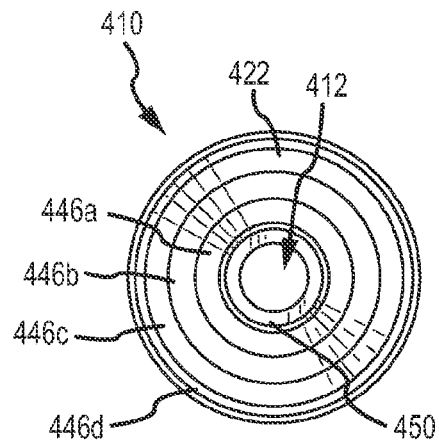
FIG. 9B is a top plan view of the nozzle illustrated in FIG. 9A.
Figure 9C:
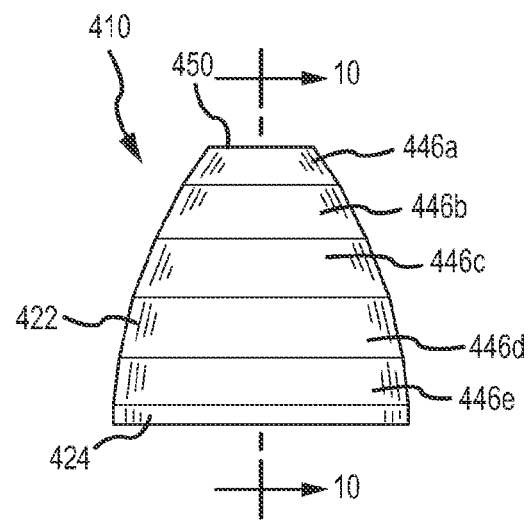
FIG. 9C is a side elevation view of the nozzle illustrated in FIG. 9A.
Figure 9D:
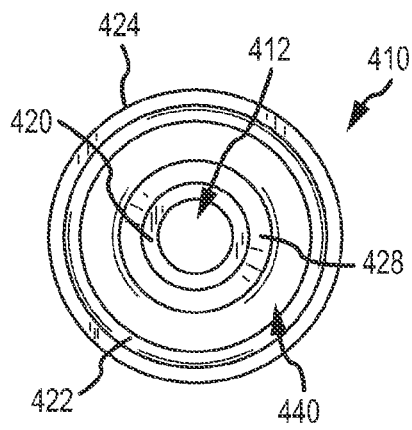
FIG. 9D is a bottom plan view of the nozzle illustrated in FIG. 9A.
Figure 9E:
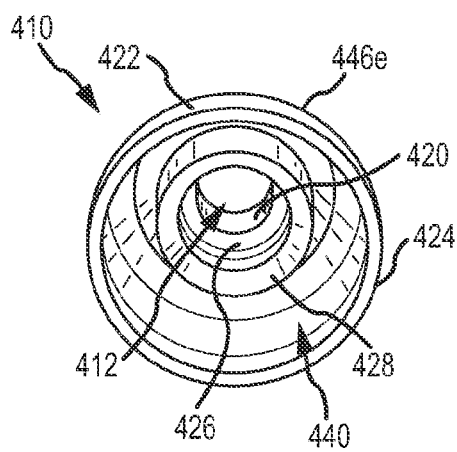
FIG. 9E is a bottom isometric view of the nozzle illustrated in FIG. 9A.
Figure 10:
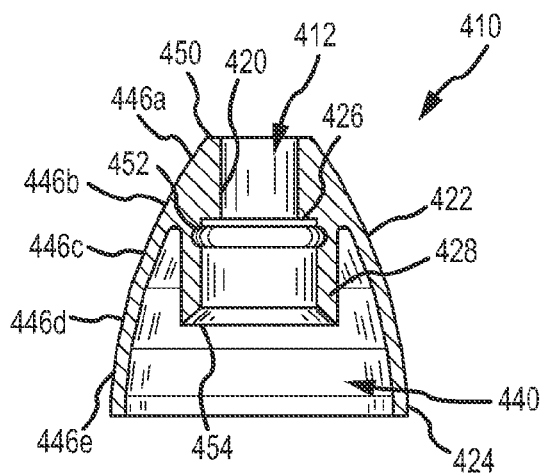
FIG. 10 is a cross-section view of the nozzle illustrated in FIG. 9A, viewed along line 10-10 in FIG. 9B.

FIG. 9A is a top isometric view of the faceted nozzle 410. FIG. 9B is a top plan view of the faceted nozzle 410. FIG. 9C is a side elevation view of the faceted nozzle 410. FIG. 9D is a bottom plan view of the faceted nozzle 410. FIG. 9E is a bottom isometric view of the faceted nozzle 410. FIG. 10 is a cross-section view of the faceted nozzle 410, as indicated by line 10-10 in FIG. 9C. Referring to FIGS. 9A-10, the faceted nozzle 410 is self-sealing and may be made of a soft elastomeric material, for example, food grade silicone rubber. The nozzle 410 includes a tip 450 or apex which is the first portion of the nozzle 410 to enter the user's nostril when attached to the vessel 100, 101. An outlet aperture 412 is formed in a center portion of the tip 450.

A skirt 422 or body is formed by a wall extending downwardly and away from the tip 450, as can be see from FIG. 9A, the skirt 422 is faceted or stepped circumferentially, or otherwise made up of regions having flat extensions or mixed flat and curved extensions, as the skirt 422 extends downwards. In some exemplary implementations the skirt 422 may have a wall thickness of approximately 0.040 inches.

The skirt 422 of the faceted nozzle 410 acts to form a seal with the user's nostril when the faceted nozzle 410 is attached to the vessel 100, 101. The skirt 422 includes steps 446a-446e, which create ridges on the outer surface of the skirt 422. In some implementations the steps 446a-446e may be approximately the same height; however each step 446a-446e may have a different average or center diameter. In these implementations, each step 446a-446e increases the overall outer diameter of the skirt 422 and the faceted nozzle 410 maintains a generally rounded shape. For example, the first step 446a has a smaller average diameter than the second step 446b, and so on. In other implementations the steps 446a-446e may have different widths, such that the first step 446a may cover a greater portion of the outer surface of the skirt 422 than the second step 446b.

For example, as can been seen in FIG. 9A, the steps 446a-446e may be a series of stacked frustums having different outer wall angles. Each step 446a-446e is sloped at a predetermined angled and the outer wall has a larger diameter at the bottom edge of the steps 446a-446e than at the top edge of each step 446a-446e. In these implementations, each step 446a-446e decreases in diameter from the bottom edge to the top edge. Additionally, each step 446a-446e may have a different average diameter than the preceding step 446a-446e. This is because each step 446a-446e may have a different outer wall angle than the previous step 446a-446e. In some embodiments, the configuration of stacked frustum sections on top of one another may include ridges between each of the steps 446a-446e at the point of transition, from one step 446a-446e to the next, this gives the skirt 422 a faceted appearance and feel.

In these implementations, the user inserts the tip 450 into a user's nostril and then tips the vessel 100, 101, allowing the solution to travel from the main body 120 to the end portion 148 of the spout 124. Once the nasal solution enters the end portion 148, the solution enters the inner collar 428 proximate the tip 450 and exits into the nasal cavity via the outlet aperture 412. As the faceted nozzle 410 creates a seal between the nostril wall and the skirt 422 via the facets or steps 446a-446e, the nasal solution is deposited into the nasal cavity without substantially leaking around the faceted nozzle 410 and the user's nostril.

While the tip 450 is inserted into a user's nostril, one of the steps 446a-446e creates a seal between the faceted nozzle 410 and the nostril walls. The particular step 446a-446e that engages the user's nostril depends upon the size of the user's nostril. For example, the larger the user's nostril the lower the step 446a-446e may be that engages the nostril wall. The steps 446a-446e create a better seal than a purely rounded nozzle, as the steps 446a-446e better conform to the nostril wall—the nostril wall is not purely oval-shaped or conical-shaped—and the steps 446a-446e better mimic the inner surface of the nostril wall. It should be noted that although five steps 446a-446e have been illustrated, any number of steps 446a-446e may be included. The number of steps 446a-446e may be altered to create a smoother or rougher skirt 422. For example, depending on the desired sealing level the number of steps 446a-446e may be increased or decreased.

The skirt 422, when positioned in the user's nasal passage, flexes inwardly into the void 440 formed as the skirt 422 extends away from the connection between the faceted nozzle 410 and the second portion 198 of the end portion 148. As the skirt 422 flexes when sealing with the user's nostril, it may do so radially and/or irregularly around its circumference in order to closely match the shape of the user's nostril. This helps create an adequate seal between the users nostril and the faceted nozzle 410 structure. When the faceted nozzle 410 is removed from the user's nostril, the elastomeric material of the skirt 422 springs back into its original shape. Additionally, the gently curving, cone-like shape of the faceted nozzle 410 from the tip 450 down to the terminal edge 424 of the skirt 422 allows for a close fit with a variety of sizes of nasal passages.

The skirt 422 terminates at a terminal edge 424. In some embodiments the terminal edge 424 may be a continuation of the steps 446a-446e and in other embodiments the terminal edge 424 may extend past the steps 446a-446e creating a shoulder, flange, or the like. In these embodiments, the faceted nozzle 410 may be substantially free-standing along the skirt 422, i.e., the skirt 422 and/or other outer surfaces of the faceted nozzle 410 may be substantially unrestricted. As can be seen from FIG. 8, the terminal edge 424 is unrestricted by the first portion 194 of the end portion 148 of spout 124.

A variety of embodiments and variations of structures and methods are disclosed herein. Where appropriate, common reference numbers were used for common structural and method features. However, unique reference numbers were sometimes used for similar or the same structural or method elements for descriptive purposes. As such, the use of common or different reference numbers for similar or the same structural or method elements is not intended to imply a similarity or difference beyond that described herein.

The references herein to "up" or "top", "bottom" or "down", "lateral" or "side", and "horizontal" and "vertical", as well as any other relative position descriptor are given by way of example for the particular embodiment described and not as a requirement or limitation of the vessel or the apparatus and method for assembling the vessel. Reference herein to "is", "are", "should", "would", or other words implying a directive or positive requirement are intended to be inclusive of the permissive use, such as "may", "might", "could" unless specifically indicated otherwise.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A vessel for use in rinsing a user's nasal passage comprising
    a main body having an exterior surface;
    a spout extending off the main body;
    an elastomeric nozzle attached to the spout, the elastomeric nozzle defining an outer skirt having a free end and being deflectable upon engagement with the walls of the user's nasal cavity;
    the main body having gripping indentations along opposing sidewalls thereof; and
    a vacuum breaker valve formed in a top portion of the main body for manual actuation by the user to control the flow of a fluid positioned in the vessel out of the nozzle, the vacuum breaker valve comprising
        a valve body; and
        a top flange that extends downward and outward from a top potion of the valve body and engages the exterior surface of the main body to operate as a biasing mechanism for the valve body by maintaining the valve body in a closed position; wherein
        to move the vacuum breaker valve to an open position, the valve body is downwardly compressed by a user, causing the of the top flange to splay outward and slide along the exterior surface of the main body; and in the open position the vacuum breaker valve allows airflow into the main body to provide a constant fluid flow out of the elastomeric nozzle.

2. The vessel of claim 1, wherein the outer skirt comprises a faceted outer surface.

3. The vessel of claim 2, wherein the outer skirt is comprised of at least two frustum sections stacked in series on top of one other, wherein a first frustum section has an average larger diameter than a second frustum section.

4. The vessel of claim 1, wherein the valve is in a closed position until actuation by the user.

5. The vessel of claim 1, wherein the valve comprises an aperture formed in the main body and the valve body is arranged in the aperture.

6. The vessel of claim 5, wherein the top flange defines one or more flange openings proximate the aperture, and when the vacuum breaker valve is actuated, air enters into an interior of the main body by passing through the one or more flange openings and the valve aperture.

7. The vessel of claim 5, wherein the valve body comprises a bottom flange arranged within an interior of the main body, wherein the bottom flange engages with an interior surface of the main body surrounding the aperture and forms a seal between the valve body and the main body in the closed position.

8. The vessel of claim 7, wherein the bottom flange disengages with the interior surface of the main body upon actuation of the valve and allows air to flow through the aperture into the interior of the main body.

9. The vessel of claim 5, wherein the valve body further comprises
    at least two ribs extending longitudinally along an outer surface of the valve body; and
    a sealing flange extending from a lower portion of the valve body; wherein
    the valve body extends through the aperture formed in the main body; and
    the sealing flange selectively engages an interior surface of the main body.

10. The vessel of claim 5, wherein the valve body further comprises
    a plurality of ribs extending longitudinally along an outer surface of the valve body, wherein the plurality of ribs define channels therebetween along the valve body and assist in maintaining an alignment of the valve body within the aperture of the main body; and
    a sealing flange extending from a lower portion of the valve body and positioned in an interior of the main body; wherein
    in the closed position the sealing flange seats in a valve seat recessed into an interior surface of the main body and forms a seal between the valve body and the main body; and
    in the open position the sealing flange disengages from the valve seat to define a fluid flow pathway between the sealing flange and the aperture in the main body through the channels between the ribs.

11. The vessel of claim 10, wherein when the valve body is downwardly compressed, the valve body and the sealing flange move vertically downward and the sealing flange moves further into the interior of the main body.

12. The vessel of claim 1, wherein the nozzle and the spout are detachably coupled.

13. The vessel of claim 1, wherein the spout forms a conical section that tapers down as the spout extends towards a spout portion forming a spout aperture, and the outer skirt free end is deflectable into a void space formed between the conical section and the outer skirt.

14. The vessel of claim 1, wherein the top flange has a substantially conical shape.

15. The vessel of claim 1, wherein the main body is sufficiently rigid to resist deformation when a user grips the main body.

16. The vessel of claim 1, wherein
the valve body comprises a bottom flange extending into an interior of the main body;
the main body comprises a valve seat recessed in an interior surface of the main body;
in the closed position the bottom flange seats in the valve seat and forms a seal between the valve body and the main body; and
in the open position the bottom flange disengages from the valve seat to allow airflow into the main body.

17. The vessel of claim 16, wherein the main body further comprises a raised platform defined on the exterior surface and the top flange sits on top of and engages the raised platform.

18. A vessel for use in rinsing a user's nasal passage comprising
a main body defining an exterior surface;
a spout extending off a front portion the main body, wherein the spout is integrally formed with the main body;
an elastomeric nozzle detachably coupled to the spout, the elastomeric nozzle defining an outer skirt having a free end and being deflectable upon engagement with the walls of the user's nasal cavity; and
a vacuum breaker valve formed in a top portion of the main body for manual actuation by the user to control the flow of a fluid positioned in the vessel out of the nozzle, the vacuum breaker valve comprising a valve body that engages the exterior of the main body, the valve body comprising
a user engagement surface;
a flange wall extending downward and outward at an angle from the user engagement surface; wherein
to move the vacuum breaker valve to an open position, a user vertically compresses the user engagement surface, causing the valve body to move vertically relative to the main body and causing the flange wall to splay outward and slide along the exterior surface of the main body; and
in the open position the valve allows airflow into the main body and allows the fluid to flow in a constant stream from the main body through the elastomeric nozzle when a user tilts the main body.

19. The vessel of claim 18, wherein the outer skirt comprises a faceted outer surface having at least two frustum sections stacked in series on top of one another, wherein a first frustum section has an average larger diameter than a second frustum section.

20. The vessel of claim 19 wherein the spout forms a conical section that tapers down as the spout extends towards a spout portion forming a spout aperture, and the outer skirt free end is deflectable into a void space formed between the conical section and the outer skirt.

21. The vessel of claim 20, wherein the nozzle further comprises an inner collar for coupling to an external circumference of the spout portion forming the spout aperture, wherein the inner collar forms a nozzle aperture such that fluid positioned in the vessel flows from the spout aperture out the nozzle through the nozzle aperture.

22. The vessel of claim 18, further comprising an aperture formed in a back portion of the main body opposite the front portion and a cap configured to be received on the aperture, wherein the aperture is configured as a vessel inlet.

23. The vessel of claim 22, wherein when the cap is received on the aperture, the cap and the aperture form a water-tight seal.

24. The vessel of claim 18, wherein at least two apertures are defined through the flange wall and are spaced apart from each other.

25. The vessel of claim 24, wherein aperture sidewalls defining the at least two apertures are oriented substantially perpendicular with respect to a top surface of the main body.

* * * * *